(12) United States Patent
Liu et al.

(10) Patent No.: US 11,841,304 B1
(45) Date of Patent: Dec. 12, 2023

(54) DEVICE AND METHOD FOR TESTING EFFECTIVE DIFFUSION COEFFICIENT OF HELIUM IN HELIUM-BEARING NATURAL GAS

(71) Applicant: Peking University, Beijing (CN)

(72) Inventors: Quanyou Liu, Beijing (CN); Pengpeng Li, Beijing (CN); Yu Gao, Beijing (CN)

(73) Assignee: Peking University, Beijing (CN)

( * ) Notice: Subject to any disclaimer, the term of this patent is extended or adjusted under 35 U.S.C. 154(b) by 0 days.

(21) Appl. No.: 18/223,568

(22) Filed: Jul. 19, 2023

(30) Foreign Application Priority Data

Nov. 23, 2022 (CN) .......................... 202211472621.0

(51) Int. Cl.
*G01N 13/00* (2006.01)
*G01N 30/88* (2006.01)

(52) U.S. Cl.
CPC ............ *G01N 13/00* (2013.01); *G01N 30/88* (2013.01); *G01N 2013/003* (2013.01)

(58) Field of Classification Search
CPC ... G01N 13/00; G01N 13/88; G01N 2013/003
See application file for complete search history.

(56) References Cited

U.S. PATENT DOCUMENTS

2020/0309711 A1* 10/2020 Yang .................... G01B 11/165

FOREIGN PATENT DOCUMENTS

| AU | 2020103877 | A4 | 2/2021 |
|---|---|---|---|
| CN | 1773246 | A | 5/2006 |
| CN | 102980837 | A | 3/2013 |
| CN | 103206210 | A | 7/2013 |
| CN | 103674679 | A | 3/2014 |
| CN | 104897525 | A | 9/2015 |
| CN | 105092419 | A | 11/2015 |
| CN | 108414419 | * | 8/2018 |

* cited by examiner

*Primary Examiner* — Jamel E Williams
*Assistant Examiner* — Alex T Devito
(74) *Attorney, Agent, or Firm* — Bayramoglu Law Offices LLC

(57) ABSTRACT

A device and method for testing an effective diffusion coefficient of helium in helium-bearing natural gas solves the problem that there is currently no systematic method or supporting experimental device to quantitatively characterize the diffusion behavior of helium in helium-bearing natural gas. The device includes a diffusion system and a gas sampling and analysis system. The diffusion system includes an upstream diffusion chamber, a downstream diffusion chamber, and a true triaxial apparatus, and is configured to simulate a gas diffusion process. The gas sampling and analysis system includes an upstream gas sample retention chamber, a downstream gas sample retention chamber, and a chromatographic analyzer, and is configured to sample a diffusing gas and analyze composition of the gas. By performing diffusion process simulation, gas sampling and analysis, and data calculation and fitting, the effective diffusion coefficient of helium in the helium-bearing natural gas is finally acquired.

9 Claims, 5 Drawing Sheets

DEVICE AND METHOD FOR TESTING EFFECTIVE DIFFUSION COEFFICIENT OF HELIUM IN HELIUM-BEARING NATURAL GAS

CROSS REFERENCE TO THE RELATED APPLICATIONS

This application is based upon and claims priority to Chinese Patent Application No. 202211472621.0, filed on Nov. 23, 2022, the entire contents of which are incorporated herein by reference.

TECHNICAL FIELD

The present disclosure relates to the technical field of helium survey and detection equipment, and in particular to a device and method for testing an effective diffusion coefficient of helium in helium-bearing natural gas.

BACKGROUND

As a trace component, helium is usually associated with gaseous hydrocarbon components (mainly $CH_4$), $CO_2$, and $N_2$ to form reservoirs. Helium has a kinetic diameter of 0.26 nm, which is significantly smaller than that of $CH_4$, $CO_2$, and $N_2$ (0.38 nm, 0.33 nm, and 0.364 nm, respectively). This indicates that helium has the strongest diffusion ability. Helium diffusion is one of the main causes of helium reservoir damage. Currently, there is no systematic method or supporting experimental device to quantitatively characterize the diffusion behavior of helium in helium-bearing natural gas. Thus, the understanding of reservoir formation theory and resource potential assessment of helium is limited.

SUMMARY

An objective of the present disclosure is to provide a device and method for testing an effective diffusion coefficient of helium in helium-bearing natural gas. The present disclosure solves the problem that there is currently no systematic method or supporting experimental device to quantitatively characterize the diffusion behavior of helium in helium-bearing natural gas.

To solve the above technical problem, the present disclosure provides the following technical solutions.

The device for testing an effective diffusion coefficient of helium in helium-bearing natural gas includes: a diffusion system and a gas sampling and analysis system, where the diffusion system includes an upstream diffusion chamber, a downstream diffusion chamber, and a true triaxial apparatus; two ends of the true triaxial apparatus are respectively connected to the upstream diffusion chamber and the downstream diffusion chamber; the upstream diffusion chamber is filled with argon, and the downstream diffusion chamber is filled with helium-bearing natural gas for simulating an actual environment; the true triaxial apparatus is configured to accommodate a rock core, apply a load to the rock core, and simulate a formation temperature; the gas sampling and analysis system includes an upstream gas sample retention chamber, a downstream gas sample retention chamber, and a chromatographic analyzer; the upstream gas sample retention chamber is connected to the upstream diffusion chamber to sample the gas in the upstream diffusion chamber; the downstream gas sample retention chamber is connected to the downstream diffusion chamber to sample the gas in the downstream diffusion chamber; an initial state of the upstream gas sample retention chamber and the downstream gas sample retention chamber is a vacuum state for convenience of gas sampling; and the chromatographic analyzer is configured to analyze gas composition in the upstream gas sample retention chamber and the downstream gas sample retention chamber.

Further, the device for testing an effective diffusion coefficient of helium in helium-bearing natural gas includes a pressure difference balancing argon cylinder and an environmental simulation gas supply cylinder, where the pressure difference balancing argon cylinder is connected to the upstream diffusion chamber to inject the argon into the upstream diffusion chamber; and the environmental simulation gas supply cylinder is connected to the downstream diffusion chamber to inject the helium-bearing natural gas for simulating the actual environment into the downstream diffusion chamber.

Further, the diffusion system includes a differential pressure sensor; and two ends of the differential pressure sensor are respectively connected to the upstream diffusion chamber and the downstream diffusion chamber to detect a gas pressure difference between the upstream diffusion chamber and the downstream diffusion chamber.

Further, the diffusion system includes a transfer tube and a first control valve; the transfer tube is connected in parallel with the differential pressure sensor; two ends of the transfer tube are respectively connected to the upstream diffusion chamber and the downstream diffusion chamber; and the first control valve is provided on the transfer tube to control switching-on/off of the transfer tube.

Further, the device for testing an effective diffusion coefficient of helium in helium-bearing natural gas includes a second control valve and a third control valve, where the second control valve is provided between the upstream diffusion chamber and the upstream gas sample retention chamber to control switching-on/off of the upstream diffusion chamber and the upstream gas sample retention chamber; and the third control valve is provided between the downstream diffusion chamber and the downstream gas sample retention chamber to control switching-on/off of the downstream diffusion chamber and the downstream gas sample retention chamber.

Further, the device for testing an effective diffusion coefficient of helium in helium-bearing natural gas includes a vacuum pump, where the vacuum pump is connected to the diffusion system and the gas sampling and analysis system to vacuumize the diffusion system, the gas sampling and analysis system, and a connecting tube.

Further, the true triaxial apparatus includes pressure plates, sealing strips, and an electric heating wire; the pressure plates are abutted against the rock core to apply a pressure to the rock core; adjacent pressure plates are separated by the sealing strip; the pressure plates and the sealing strips enclose a rock core accommodation chamber; and the electric heating wire is provided at a side of the pressure plate away from the rock core to adjust a temperature of the rock core.

Further, the device for testing an effective diffusion coefficient of helium in helium-bearing natural gas includes a first booster pump; the true triaxial apparatus further includes a pressure block and a hydraulic bag; the pressure block includes one end connected to the pressure plate and the other end connected to the hydraulic bag; and the first booster pump is connected to the hydraulic bag to drive the hydraulic bag to expand, so as to push the pressure block to move towards the rock core.

Further, the gas sampling and analysis system includes a chromatographic carrier gas cylinder; the chromatographic carrier gas cylinder is connected to the upstream gas sample retention chamber, the downstream gas sample retention chamber and the chromatographic analyzer to carry the gas in the upstream gas sample retention chamber and the gas in the downstream gas sample retention chamber into the chromatographic analyzer.

Another aspect of the present disclosure provides a method device for testing an effective diffusion coefficient of helium in helium-bearing natural gas, using the device for testing an effective diffusion coefficient of helium in helium-bearing natural gas, and including the following steps:

rock core loading: putting the rock core into the true triaxial apparatus; applying a pressure, and maintaining the pressure; and adjusting a temperature of the rock core to a test temperature, and keeping the temperature constant;

vacuumizing: starting the vacuum pump to vacuumize the diffusion system, the gas sampling and analysis system, and the connecting tube;

gas injection: opening the pressure difference balancing argon cylinder to inject the argon into the upstream diffusion chamber; opening the environmental simulation gas supply cylinder to inject the helium-bearing natural gas for simulating the actual environment into the downstream diffusion chamber; and closing the pressure difference balancing argon cylinder and the environmental simulation gas supply cylinder when gas pressures in the upstream diffusion chamber and the downstream diffusion chamber reach a preset value;

gas diffusion: communicating the upstream diffusion chamber, the downstream diffusion chamber, and the true triaxial instrument; and allowing, under the action of a concentration gradient, the argon in the upstream diffusion chamber to diffuse through the rock core to the downstream diffusion chamber and the helium-bearing natural gas in the downstream diffusion chamber to diffuse through the rock core to the upstream diffusion chamber;

gas sampling and analysis: turning, during a diffusion process, the vacuum pump on to vacuumize the upstream gas sample retention chamber and the downstream gas sample retention chamber, and then turning the vacuum pump off; turning the second control valve on to allow the gas in the upstream diffusion chamber to enter the upstream gas sample retention chamber, and turning the third control valve on to allow the gas in the downstream diffusion chamber to enter the downstream gas sample retention chamber; then, turning the second control valve and the third control valve off; analyzing, through the chromatographic analyzer, compositions of a mixed gas in the upstream gas sample retention chamber and compositions of the mixed gas in the downstream gas sample retention chamber, respectively; and repeating this step at least five times to acquire at least five groups of data on the compositions of the mixed gas, where the data, acquired at last two times, on the compositions of the mixed gas are identical; and diffusion coefficient calculation: calculating, according to Fick's second law, an effective diffusion coefficient $D_i$ of an i-th gas in the helium-bearing natural gas as follows:

$$D_i = a \frac{L}{A} \left( \frac{1}{1/V_{upstream} + 1/V_{downstream}} \right) \quad (1)$$

wherein,

L denotes a length of the rock core;

A denotes a cross-sectional area of the rock core;

$V_{upstream}$ denotes a volume of the upstream diffusion chamber;

$V_{downstream}$ denotes a volume of the downstream diffusion chamber;

α denotes a concentration decline index of the i-th gas, calculated as follows:

$$a = \ln\left(\frac{\Delta C_0}{\Delta C_t}\right)/\Delta t, \quad (2)$$

where, $\Delta C_0$ denotes a concentration difference of the i-th gas in the upstream diffusion chamber and the downstream diffusion chamber at a time $t_0$ during the diffusion process;

$\Delta C_t$ denotes a concentration difference of the i-th gas in the upstream diffusion chamber and the downstream diffusion chamber at a time t during the diffusion process; and $\Delta t$ denotes a diffusion time, $\Delta t = t - t_0$;

in the diffusion process, a natural logarithm of a ratio of the concentration difference at the initial time $t_0$ to the concentration difference at the time t is linear with the diffusion time $\Delta t$;

therefore, according to equations (1) and (2), $$\ln\left(\frac{\Delta C_0}{\Delta C_t}\right) = D_i E t - D_i E t_0, \quad (3)$$

where, $E = A(1/V_{upstream} + 1/V_{downstream})/L$ is a constant;

according to equation (3), a slope k is acquired by fitting through a least squares method; and finally, the effective diffusion coefficient of the i-th gas in the helium-bearing natural gas is $D_i = k/E$.

Based on the above technical solutions, the present disclosure achieves the following technical effects.

The device for testing an effective diffusion coefficient of helium in helium-bearing natural gas includes: a diffusion system and a gas sampling and analysis system, where the diffusion system includes an upstream diffusion chamber, a downstream diffusion chamber, and a true triaxial apparatus; two ends of the true triaxial apparatus are respectively connected to the upstream diffusion chamber and the downstream diffusion chamber; the upstream diffusion chamber is filled with argon, and the downstream diffusion chamber is filled with helium-bearing natural gas for simulating an actual environment; the true triaxial apparatus is configured to accommodate a rock core, apply a load to the rock core, and simulate a formation temperature; the gas sampling and analysis system includes an upstream gas sample retention chamber, a downstream gas sample retention chamber, and a chromatographic analyzer; the upstream gas sample retention chamber is connected to the upstream diffusion chamber to sample the gas in the upstream diffusion chamber; the downstream gas sample retention chamber is connected to the downstream diffusion chamber to sample the gas in the downstream diffusion chamber; an initial state of the upstream gas sample retention chamber and the downstream gas sample retention chamber is a vacuum state for convenience of gas sampling; and the chromatographic analyzer is configured to analyze gas composition in the upstream gas sample retention chamber and the downstream gas sample retention chamber.

In the present disclosure, the diffusion system simulates a diffusion process of the helium-bearing natural gas in a formation, and the true triaxial apparatus simulates a formation pressure and temperature. The gas pressure inside the upstream diffusion chamber is equal to that inside the downstream diffusion chamber, so as to ensure accurate simulation of the diffusion process, thereby acquiring accurate diffusion data. During the diffusion process, the helium-bearing natural gas in the downstream diffusion chamber enters the upstream diffusion chamber through the rock core, and the argon in the downstream diffusion chamber enters the downstream diffusion chamber through the rock core, achieving diffusion equilibrium. The gas sampling and analysis system repeatedly samples the gas from the upstream diffusion chamber and the downstream diffusion chamber at certain intervals, and analyzes the gas composition in the upstream diffusion chamber and the downstream diffusion chamber through the chromatographic analyzer to acquire multiple groups of gas composition data.

Finally, the present disclosure calculates and fits the acquired gas composition data to acquire the effective diffusion coefficient of helium in the helium-bearing natural gas.

The present disclosure simulates the diffusion process of helium-bearing natural gas in a geological environment through the diffusion system, and acquires gas samples for analysis through the gas sampling and analysis system during the diffusion process. Finally, the present disclosure calculates the effective diffusion coefficient of the helium in helium-bearing natural gas. Therefore, the present disclosure provides a comprehensive device for calculating the diffusion coefficient of helium in helium-bearing natural gas, quantitatively characterizing the diffusion behavior of helium in helium-bearing natural gas.

BRIEF DESCRIPTION OF THE DRAWINGS

To describe the technical solutions in the specific implementations of the present disclosure or the prior art more clearly, the accompanying drawings required for describing the specific implementations or the prior art are briefly described below. Apparently, the accompanying drawings in the following description show merely some implementations of the present disclosure, and a person of ordinary skill in the art may still derive other accompanying drawings from these accompanying drawings without creative efforts.

Figure 1:
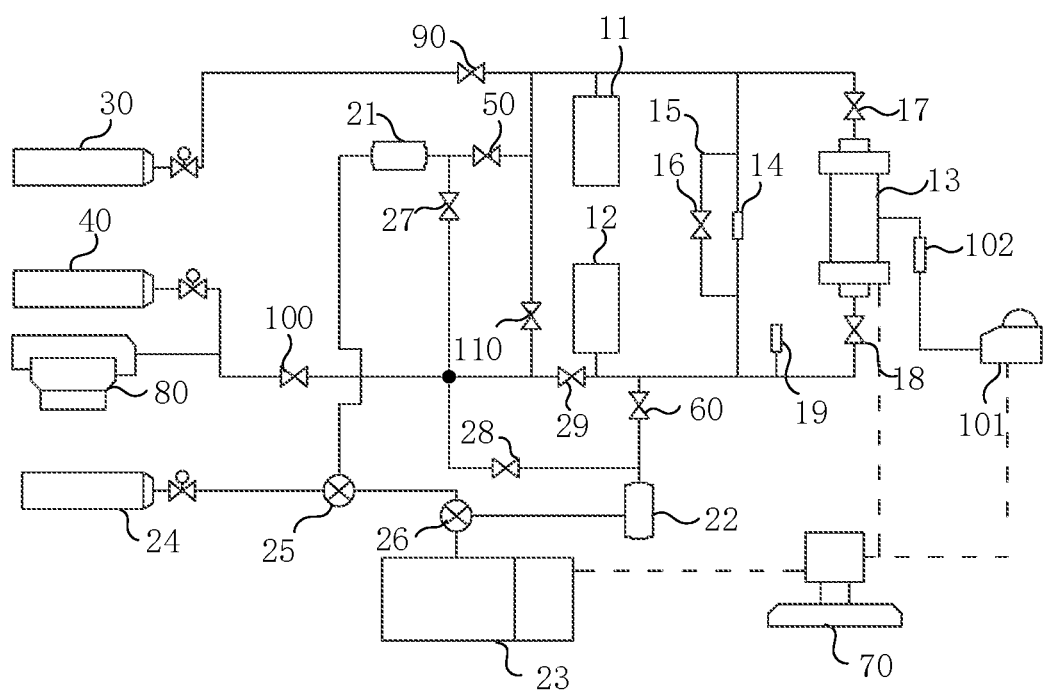
FIG. 1 is a structural diagram of a device for testing an effective diffusion coefficient of helium in helium-bearing natural gas according to an embodiment of the present disclosure.

Reference Numerals: 11. upstream diffusion chamber; 12. downstream diffusion chamber; 13. true triaxial apparatus; 14. differential pressure sensor; 15. transfer tube; 16. first control valve; 17. first switch valve; 18. second switch valve; 19. first pressure sensor; 101. first booster pump; 102. load pressure gauge; 21. upstream gas sample retention chamber; 22. downstream gas sample retention chamber; 23. chromatographic analyzer; 24. chromatographic carrier gas cylinder; 25. first three-way valve; 26. second three-way valve; 27. third switch valve; 28. fourth switch valve; 29. fifth switch valve; 30. pressure difference balancing argon cylinder; 40. environmental simulation gas supply cylinder; 50. second control valve; 60. third control valve; 70. data processing module; 80. vacuum pump; 90. first gas cylinder control valve; 100. second gas cylinder control valve; and 110. fourth control valve;

131. bearing frame; 132. pressure chamber; 133. hydraulic bag; 134. pressure block; 135. pressure plate; 136. sealing strip; 137. second pressure sensor; 138. temperature sensor; 139. electric heating wire; 130. hydraulic cylinder; 1301. guide post; 1302. driving circuit; 1303. through-hole; 1304. guide hole; 1361. arc segment; 1362. positioning segment; 1363. reinforced sealing segment; and 1364. deformation cavity;

221. air vortex tube; 222. air pump; 223. heat exchange tube; 224. multi-way valve; 225. branch tube; and 226. header tube; and

111. gas storage cylinder; 112. helium sensor; 113. first gas pressure sensor; 114. temperature and humidity sensor; 115. negative pressure pump; and 116. distribution tube.

DETAILED DESCRIPTION OF THE EMBODIMENTS

In order to make the objectives, technical solutions and advantages of the embodiments of the present disclosure clearer, the technical solutions in the embodiments of the present disclosure will be clearly and completely described below in conjunction with the drawings in the embodiments of the present disclosure. Obviously, the described embodiments are some, rather than all of the embodiments of the present disclosure. Generally, the components of the embodiments of the present disclosure described and shown in the drawings may be arranged and designed in various manners.

Therefore, the following detailed description of the embodiments of the present disclosure in the drawings is not intended to limit the protection scope of the present disclosure, but merely represent selected embodiments of the present disclosure. All other embodiments obtained by those of ordinary skill in the art based on the embodiments of the present disclosure without creative efforts should fall within the protection scope of the present disclosure.

The following describes in detail some implementations of the present disclosure with reference to the accompanying drawings. If no conflict occurs, the following embodiments and features of the embodiments may be combined with each other.

In the prior art, there is currently no systematic method or supporting experimental device to quantitatively characterize the diffusion behavior of helium in helium-bearing natural gas, which limits the understanding of reservoir formation theory and resource potential assessment of helium.

In view of this, the present disclosure provides a device for testing an effective diffusion coefficient of helium in helium-bearing natural gas. the device for testing an effective diffusion coefficient of helium in helium-bearing natural gas includes a diffusion system and a gas sampling and analysis system. The diffusion system includes upstream diffusion chamber 11, downstream diffusion chamber 12, and true triaxial apparatus 13. Two ends of the true triaxial apparatus 13 are respectively connected to the upstream diffusion chamber 11 and the downstream diffusion chamber 12. The upstream diffusion chamber 11 is filled with argon, and the downstream diffusion chamber 12 is filled with helium-bearing natural gas for simulating an actual environment. The true triaxial apparatus 13 is configured to accommodate a rock core, apply a load to the rock core, and simulate a formation temperature. The gas sampling and analysis system includes upstream gas sample retention chamber 21, downstream gas sample retention chamber 22, and chromatographic analyzer 23. The upstream gas sample retention chamber 21 is connected to the upstream diffusion chamber 11 to sample the gas in the upstream diffusion chamber 11. The downstream gas sample retention chamber 22 is connected to the downstream diffusion chamber 12 to sample the gas in the downstream diffusion chamber 12. An initial state of the upstream gas sample retention chamber 21 and the downstream gas sample retention chamber 22 is a vacuum state for convenience of gas sampling. The chromatographic analyzer 23 is configured to analyze gas composition in the upstream gas sample retention chamber 21 and the downstream gas sample retention chamber 22.

In the present disclosure, the diffusion system simulates a diffusion process of the helium-bearing natural gas in a formation, and the true triaxial apparatus 13 simulates a formation pressure and temperature. The gas pressure inside the upstream diffusion chamber 11 is equal to that inside the downstream diffusion chamber 12, so as to ensure accurate simulation of the diffusion process, thereby acquiring accurate diffusion data. During the diffusion process, the helium-bearing natural gas in the downstream diffusion chamber 12 enters the upstream diffusion chamber 11 through the rock core, and the argon in the downstream diffusion chamber 12 enters the downstream diffusion chamber 12 through the rock core, achieving diffusion equilibrium. The gas sampling and analysis system repeatedly samples the gas from the upstream diffusion chamber 11 and the downstream diffusion chamber 12 at certain intervals, and analyzes the gas composition in the upstream diffusion chamber and the downstream diffusion chamber through the chromatographic analyzer 23 to acquire multiple groups of gas composition data.

Finally, the present disclosure calculates and fits the acquired gas composition data to acquire the effective diffusion coefficient of helium in the helium-bearing natural gas.

The structure and shape of the device for testing an effective diffusion coefficient of helium in helium-bearing natural gas according to this embodiment are described in detail below with reference to FIGS. 1 to 6.

In this embodiment, the device for testing an effective diffusion coefficient of helium in helium-bearing natural gas includes a diffusion system, a gas sampling and analysis system, pressure difference balancing argon cylinder 30, environmental simulation gas supply cylinder 40, data processing module 70, and vacuum pump 80, as shown in FIG. 1.

The diffusion system is configured to simulate a diffusion process of the helium-bearing natural gas in a formation. The gas sampling and analysis system is configured to sample and analyze the gas during the diffusion process, so as to acquire calculation data and acquire the diffusion coefficient of helium. The data processing module 70 is connected to various electrical components to acquire sensor data and control an operating status of equipment. The vacuum pump 80 is configured to vacuumize a gas path of the device to ensure accurate testing. The pressure difference balancing argon cylinder 30 and the environmental simulation gas supply cylinder 40 are configured to inject the gas required for testing into the diffusion system.

Specifically, the diffusion system includes upstream diffusion chamber 11, downstream diffusion chamber 12, true triaxial apparatus 13, and differential pressure sensor 14.

Two ends of the true triaxial apparatus 13 are respectively connected to the upstream diffusion chamber 11 and the downstream diffusion chamber 12, forming a triadic series connection. The upstream diffusion chamber 11 is filled with argon, and the downstream diffusion chamber 12 is filled with helium-bearing natural gas for simulating an actual environment. The helium-bearing natural gas that simulates the actual environment is a mixed gas prepared according to the composition of the helium-bearing natural gas in the formation, for convenience of testing and use. The true triaxial apparatus 13 is configured to accommodate a rock core, apply a load to the rock core, and simulate a formation temperature, thereby simulating a diffusion condition of the helium-bearing natural gas. During the diffusion process, the argon in the upstream diffusion chamber 11 diffuses through the rock core to the downstream diffusion chamber 12 under the action of a concentration gradient. The helium-bearing natural gas that simulates the actual environment in the downstream diffusion chamber 12 diffuses through the rock core to the upstream diffusion chamber 11. It should be noted that before the diffusion begins, the pressure in the upstream diffusion chamber 11 and the downstream diffusion chamber 12 is equal. In actual testing, the upstream diffusion chamber 11 and the downstream diffusion chamber 12 have an initial gas pressure of 0.1-0.5 MPa, with a gas pressure difference of no more than 0.1 KPa.

In order to monitor the gas pressure difference, the diffusion system further includes the differential pressure sensor 14. Two ends of the differential pressure sensor 14 are respectively connected to the upstream diffusion chamber 11 and the downstream diffusion chamber 12 to detect the gas pressure difference between the upstream diffusion chamber 11 and the downstream diffusion chamber 12.

Further, in order to avoid damage caused by an excessive gas pressure difference exceeding a range of differential pressure sensor 14, the diffusion system includes transfer tube 15 and first control valve 16. Two ends of the transfer tube 15 are respectively connected to the upstream diffusion chamber 11 and the downstream diffusion chamber 12. The first control valve 16 is provided on the transfer tube 15 to control switching-on/off of the transfer tube 15. The transfer tube 15 is connected in parallel with the differential pressure sensor 14. When the gas pressure difference approaches a limit of the range, the first control valve 16 is turned on to connect the transfer tube 15. In this way, the upstream diffusion chamber 11 is communicated with the downstream diffusion chamber 12, thereby eliminating a gas pressure difference and avoiding damage to the differential pressure sensor 14.

Further, the diffusion system includes first switch valve 17 and second switch valve 18. The first switch valve 17 is located between the upstream diffusion chamber 11 and the true triaxial apparatus 13, and the second switch valve 18 is located between the downstream diffusion chamber 12 and the true triaxial apparatus 13. The first switch valve 17 and the second switch valve 18 are controlled to start a testing process. During the testing process, it is advisable to simultaneously turn on the first switch valve 17 and the second switch valve 18. The first switch valve 17 and the second switch valve 18 have a same distance to the rock core, preventing the gas in one of the diffusion chambers from entering the rock core first, and ensuring an accurate diffusion process.

In an optional solution of this embodiment, the diffusion system further includes first pressure sensor 19. The first pressure sensor 19 is configured to monitor a gas pressure in the gas path of the diffusion system and can be provided at any optional position in the diffusion system.

In an optional solution of this embodiment, the diffusion system further includes first booster pump 101 and load pressure gauge 102. The first booster pump 101 is connected to the true triaxial apparatus 13 to pressurize the true triaxial apparatus 13, such that the true triaxial apparatus 13 applies a sufficient load to the rock core. The load pressure gauge 102 is connected to the first booster pump 101 to monitor a load pressure, so as to avoid danger caused by an excessive system pressure.

Figure 2:
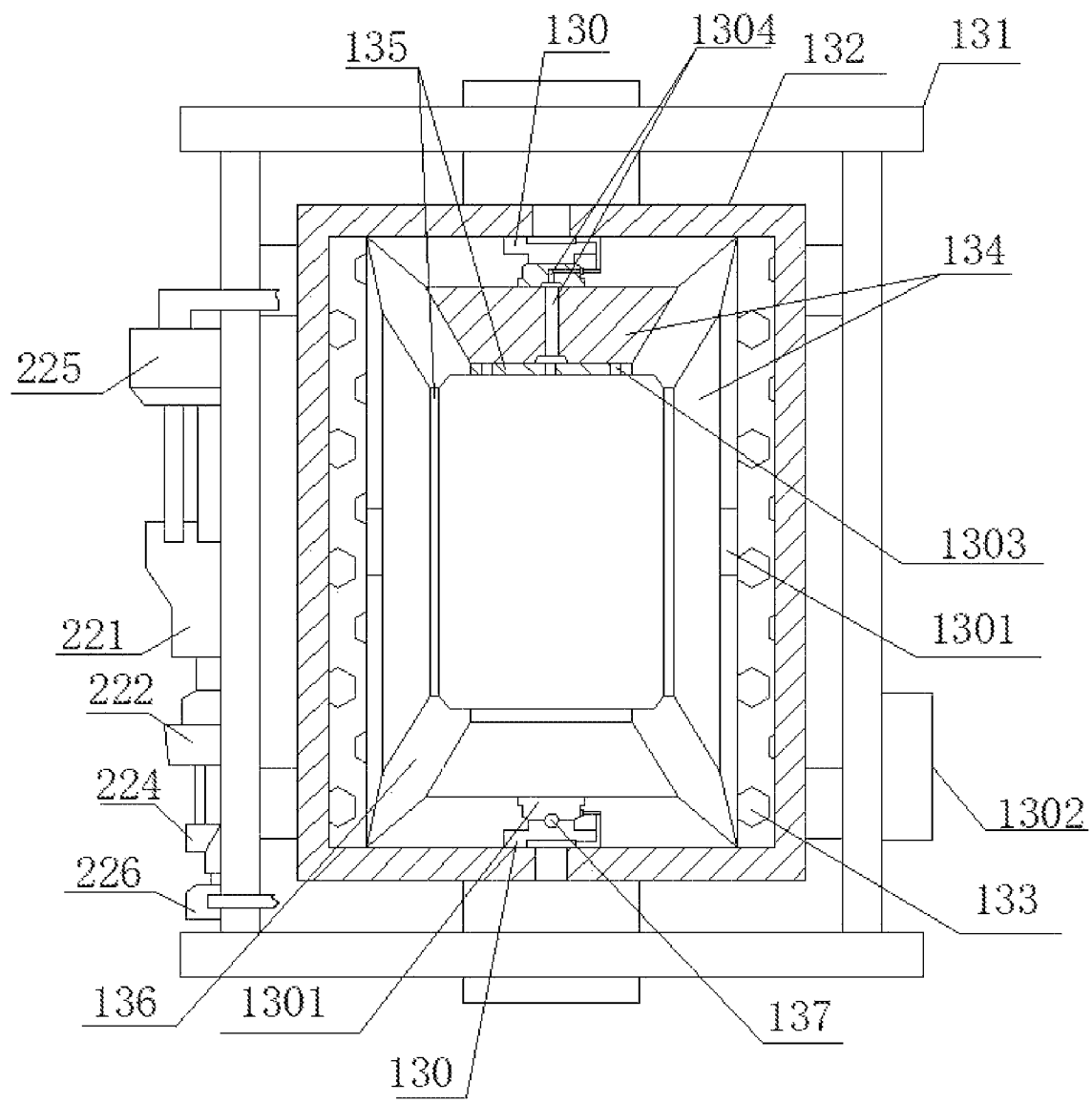
FIG. 2 is a section view of a true triaxial apparatus along a first direction.
Figure 3:
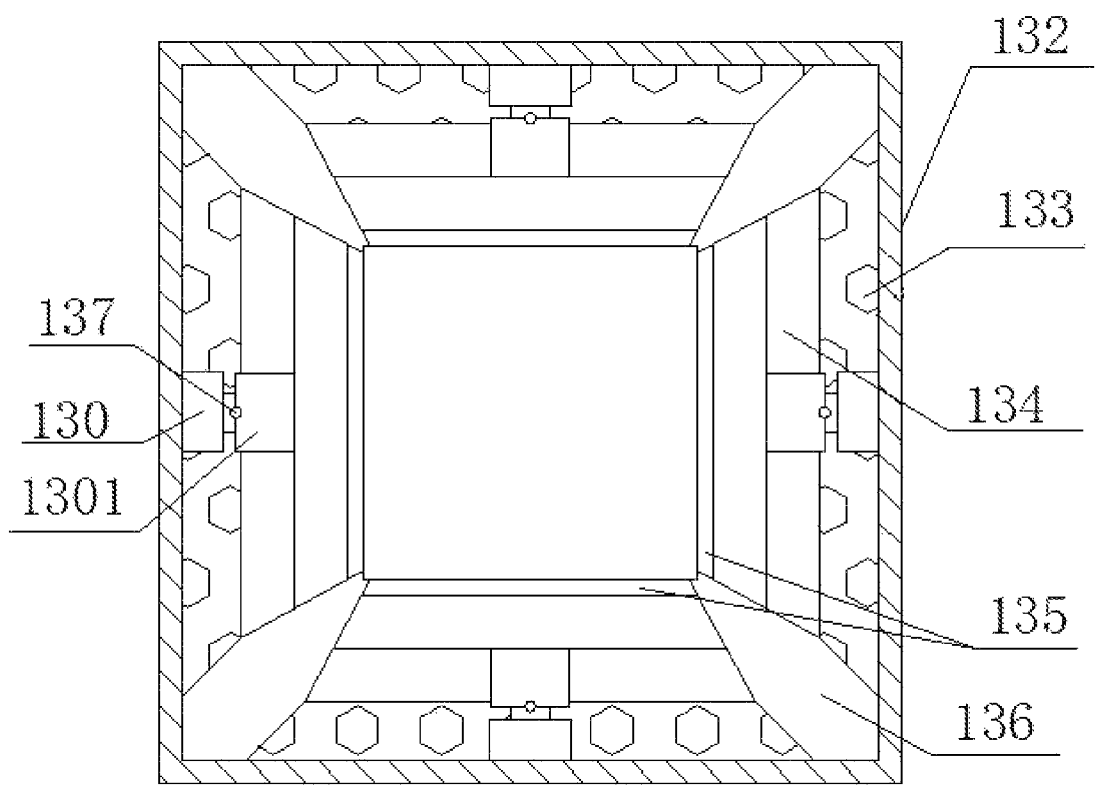
FIG. 3 is a section view of the true triaxial apparatus along a second direction.

In an optional solution of this embodiment, the true triaxial apparatus 13 includes bearing frame 131, pressure chamber 132, hydraulic bag 133, pressure blocks 134, pressure plates 135, sealing strips 136, second pressure sensor 137, temperature sensor 138, electric heating wire 139, hydraulic cylinders 130, guide post 1301, and driving circuit 1302. As shown in FIG. 2, the bearing frame 131 is a frame structure with a rectangular axial section and an axis perpendicular to a horizontal plane. The pressure chamber 132 is provided inside the bearing frame 131, and the pressure chamber 132 includes a bearing chamber and a top cover. The top cover and the bearing chamber are detachably connected to form a rock core accommodation chamber. The pressure plates 135 are provided inside the pressure chamber 132 to apply a pressure to the rock core. Specifically, there are six pressure plates 135 enclosing a rectangular space, where adjacent pressure plates 135 are separated by the sealing strip 136 to form the rock core accommodation chamber. The pressure blocks 134 are regular prismoid structures. Specifically, there are six pressure blocks 134 embedded in the pressure chamber 132. Among them, four pressure blocks 134 are arranged in an enclosed pattern, and two pressure blocks 134 are located at upper and lower ends, respectively. The pressure block 134 includes one end connected to the pressure plate 135 and the other end connected to the hydraulic cylinder 130. One end of the hydraulic cylinder 130 away from the pressure block 134 is connected to an inner wall of the pressure chamber 132. Specifically, the hydraulic cylinders 130, the pressure blocks 134, and the pressure plates 135 are distributed on a top, a bottom, a front end surface, a rear end surface, a left end surface, and a right end surface of the pressure chamber 132. The hydraulic cylinder 130 and the pressure block 134 are connected through the guide post 1301 and are distributed coaxially. The hydraulic cylinders 130 are connected in parallel with each other and are connected to the first booster pump 101 through a high-pressure tube. The hydraulic bag 133 is a hollow cylindrical structure with a rectangular axial section, and is embedded in the pressure chamber 132. The hydraulic bag 133 is provided between the pressure block 134 and the pressure chamber 132, and is communicated with the first booster pump 101 through a high-pressure tube. The first booster pump 101 drives the hydraulic bag 133, such that the hydraulic bag 133 is expanded to apply a pressure to the pressure block 134. Thus, the pressure block 134 pushes the pressure plate 135 and pressurizes the rock core. Each two adjacent pressure blocks 134 as well as the pressure block 134 and an inner surface of the pressure chamber 132 are connected by the sealing strip 136. The pressure blocks 134 are connected through the sealing strips 136 to form a closed chamber structure. The closed chamber structure provides a constant space to hold the rock core, preventing the gas from entering between a sidewall of the pressure chamber 132 and the pressure block 134, and avoiding interference with a test result due to a volume change in the gas path caused by factors such as a volume change of the hydraulic bag 133. Each of the pressure plates 135 at the top and the bottom of the pressure chamber 132 is provided with through-hole 1303. Each of the pressure block 134 and the guide post 1301 is provided with guide hole 1304. The guide hole 1304 of the pressure block 134 is communicated with the through hole 1303 and the guide hole 1304 of the guide post 1301 for gas passage. In this way, the gas can enter the upstream diffusion chamber 11 and the downstream diffusion chamber 12.

Figure 4:
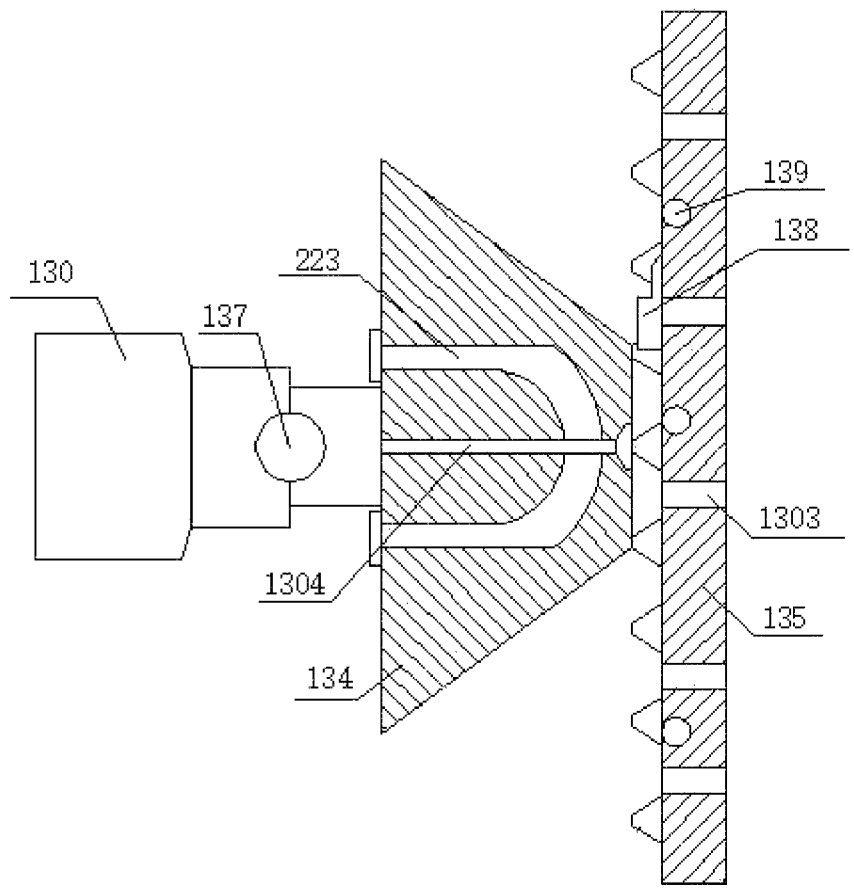
FIG. 4 is a structural diagram of a hydraulic cylinder, a pressure block, and a pressure plate.

As shown in FIG. 4, a side of the pressure plate 135 away from the rock core is provided with at least one spirally distributed electric heating wire 139 around an axis of the pressure plate 135 and at least one temperature sensor 138. The hydraulic cylinder 130 is provided at a connection position of the second pressure sensor 137 and the guide post 1301. The second pressure sensor 137, the temperature sensor 138, the electric heating wire 139, and the hydraulic cylinder 130 are all electrically connected to the driving circuit 1302. The driving circuit 1302 is connected to an outer surface of the bearing frame 131 and electrically connected to the data processing module 70.

Figure 5:
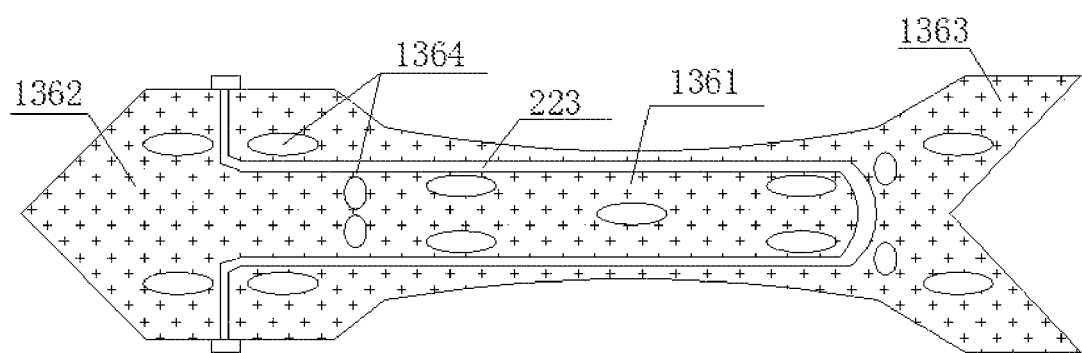
FIG. 5 is a structural diagram of a sealing strip.

Further, two adjacent sides of each two adjacent pressure blocks 134 are circular curved surfaces. The sealing strip 136 is embedded between each two adjacent pressure blocks 134 and wraps a side of the pressure block 134. As shown in FIG. 5, the sealing strip 136 includes arc segment 1361, positioning segment 1362, and reinforced sealing segment 1363. The arc segment 1361 wraps the arc sides of the two adjacent pressure blocks 134 and is slidably connected to the arc sides of the two adjacent pressure blocks. The arc segment 1361 includes a front end surface connected to the reinforced sealing segment 1363 and a rear end surface connected to the positioning segment 1362. The arc segment 1361, the positioning segment 1362, and the reinforced sealing segment 1363 are distributed coaxially. The positioning segment 1362 is a right-angle structure with an L-shaped axial section, and includes two right-angle surfaces parallel to sidewalls of the pressure chamber 132 corresponding to the two adjacent pressure blocks 134. The reinforced sealing segment 1363 is a groove structure with a right-triangle axial section. The reinforced sealing segment 1363 extends beyond the pressure block 134 and wraps a side of the pressure plate 135 close to the rock core. An edge of a right-triangle groove is flush with a surface of the pressure plate 135. The positioning segment 1362 extends beyond the pressure block 134, and is butted against and slidably connected to the inner surface of the pressure chamber 132. The pressure plates 135 are matched with the sealing strips 136 to form the rock core accommodation space. The pressure blocks 134 are matched with the sealing strips 136 to improve the sealing effect. When the pressure plate 135 and the pressure block 134 are moved, the sealing of the connection can still be ensured, ensuring that the test gas only passes through the rock core. A plurality of ellipsoidal deformation cavities 1364 parallel to an axis of the sealing strip 136 are uniformly distributed inside the arc segment 1361, the positioning segment 1362, and the reinforced sealing segment 1363. At least two ellipsoidal deformation cavities 1364 perpendicular to the axis of the sealing strip 136 are arranged at each of a connection position between one end of the arc segment 1361 and the positioning segment 1362 and a connection position between the other end of the arc segment and the reinforced sealing segment 1363. This ensures a deformation space of the sealing strip 136, increasing a contact area with the sealed part, and improving the sealing effect.

In an optional solution of this embodiment, the true triaxial apparatus 13 is also provided with a temperature control mechanism. The temperature control mechanism includes air vortex tube 221, air pump 222, heat exchange tubes 223, multi-way valve 224, branch tube 225, and header tube 226. The air vortex tube 221, the air pump 222, the multi-way valve 224, the branch tube 225, and the header tube 226 are all connected to the bearing frame 131 of the true triaxial apparatus 13. An inlet end of the air vortex tube 221 is connected to the air pump 222. The air pump 222 is connected to the header tube 226 and an external air environment through the multi-way valve 224. A low-temperature outlet port and a high-temperature outlet port of the air vortex tube 221 are connected to the branch tube 225 through a guide tube. The branch tube 225 is further connected to an inlet end of each heat exchange tube 223 through a guide tube and a control valve. The header tube 226 is connected to an outlet end of each heat exchange tube 223 through a control valve. The heat exchange tube 223 is provided with a U-shaped tubular structure. At least one heat exchange tube 223 is provided inside the pressure block 134 and the sealing strip 136. The inlet end and the outlet end of the heat exchange tube 223 are distributed from top to bottom along an axis of the pressure chamber 132, and symmetrically distributed on two sides of a midpoint of the pressure chamber 132. The air pump 222 and the multi-way valve 224 are electrically connected to the driving circuit 1302.

During use, the top cover of the pressure chamber 132 is opened, and the rock core is put into the pressure chamber. The first booster pump 101 is started to make the hydraulic cylinders 130 and the hydraulic bags 133 push the pressure plates 135, thereby squeezing and positioning the rock core. Driven by the first booster pump 101, the rock core is further pressurized to reach a stress state in the formation. Meanwhile, the electric heating wire 139 is started for heating. The temperature control mechanism regulates the temperature and keeps the temperature constant, such that the temperature of the rock core in the formation is simulated.

Figure 6:
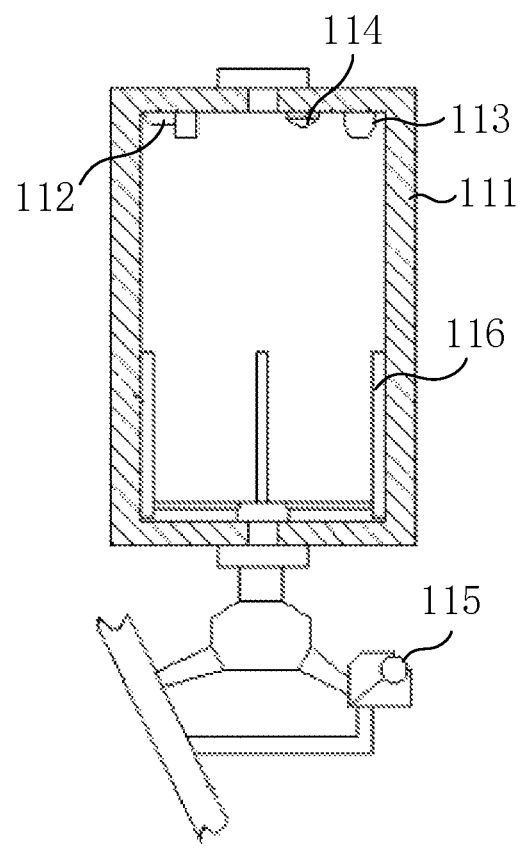
FIG. 6 is a structural diagram of an upstream diffusion chamber.

In an optional solution of this embodiment, the upstream diffusion chamber 11 is structurally identical to the downstream diffusion chamber 12. Taking the upstream diffusion chamber 11 as an example, as shown in FIG. 6, the upstream diffusion chamber 11 includes gas storage cylinder 111, helium sensor 112, gas pressure sensor, temperature and humidity sensor 114, negative pressure pump 115, and distribution tubes 116. The helium sensor 112, first gas pressure sensor 113, and the temperature and humidity sensor 114 are provided at a top of an inner chamber of the gas storage cylinder 111 to acquire environmental status information, such as helium concentration, as well as gas pressure, temperature, and humidity inside the gas storage cylinder 111. The helium sensor 112 is configured to assist in monitoring a diffusion progress and determining a sampling time. The negative pressure pump 115 is connected to the gas storage cylinder 111 through a three-way valve and can be configured to vacuumize the upstream diffusion chamber 11 so as to inject a gas into the gas storage cylinder 111. The distribution tube 116 is configured to improve gas dispersion efficiency and uniformity inside the gas storage cylinder 111.

Specifically, the gas storage cylinder 111 is a cylindrical chamber structure with a rectangular axial section. That is, the gas storage cylinder is a hollow cylinder. There are at least three distribution tubes 116 parallel to an axis of the gas storage cylinder 111 inside the gas storage cylinder 111. The distribution tubes 116 are uniformly distributed around the axis of the gas storage cylinder 111. The distribution tubes 116 are connected in parallel and communicated with each other through a three-way valve. The gas enters and exits the gas storage cylinder 111 through the distribution tubes 116 and the three-way valve. The distribution tube 116 has a height not greater than 1/2 of a height of the gas storage cylinder 111. The helium sensor 112, the first gas pressure sensor 113, the temperature and humidity sensor 114, and the negative pressure pump 115 are all electrically connected to the data processing module 70.

In an optional solution of this embodiment, the pressure difference balancing argon cylinder 30 is connected to the upstream diffusion chamber 11 to inject the argon into the upstream diffusion chamber 11. The environmental simulation gas supply cylinder 40 is connected to the downstream diffusion chamber 12 to inject the helium-bearing natural gas for simulating the actual environment into the downstream diffusion chamber 12.

Further, the device for testing an effective diffusion coefficient of helium in helium-bearing natural gas includes first gas cylinder control valve 90 and second gas cylinder control valve 100. The first gas cylinder control valve 90 is provided between the pressure difference balancing argon cylinder 30 and the upstream diffusion chamber 11, and the second gas cylinder control valve 100 is provided between the environmental simulation gas supply cylinder 40 and the downstream diffusion chamber 12. In this way, a gas injection process is controlled. The first gas cylinder control valve 90 is on during argon injection and off at other times.

In this embodiment, the gas sampling and analysis system includes upstream gas sample retention chamber 21, downstream gas sample retention chamber 22, chromatographic carrier gas cylinder 24, and chromatographic analyzer 23. The upstream gas sample retention chamber 21 is connected to the upstream diffusion chamber 11 to sample a gas in the upstream diffusion chamber 11. The downstream gas sample retention chamber 22 is connected to the downstream diffusion chamber 12 to sample a gas in the downstream diffusion chamber 12. Initial states of the upstream gas sample retention chamber 21 and the downstream gas sample retention chamber 22 are a vacuum state, for convenience of gas sampling. The chromatographic analyzer 23 is configured to analyze gas composition in the upstream gas sample retention chamber 21 and the downstream gas sample retention chamber 22. The chromatographic carrier gas cylinder 24 is connected to the upstream gas sample retention chamber 21, the downstream gas sample retention chamber 22 and the chromatographic analyzer 23 to carry the gas in the upstream gas sample retention chamber 21 and the gas in the downstream gas sample retention chamber 22 into the chromatographic analyzer 23.

In an optional solution of this embodiment, the upstream gas sample retention chamber 21 is structurally identical to the downstream gas sample retention chamber 22. Taking the upstream gas sample retention chamber 21 as an example, the upstream gas sample retention chamber 21 includes a gas bearing and storage tank, a second gas pressure sensor, a second booster pump, a piston member, and a driving airbag. The gas bearing and storage tank is a cylindrical chamber structure with a rectangular axial section. That is, the gas bearing and storage tank is a hollow cylinder. The piston member is embedded in the gas bearing and storage tank and slidably connected to an inner side of the gas bearing and storage tank. The piston member is coaxial with the gas bearing and storage tank, and divides the gas bearing and storage tank into a helium buffer chamber and a regulating chamber along an axial direction.

The driving airbag is embedded in the regulating chamber and coaxial with the gas bearing and storage tank. An upper end surface of the driving airbag is butted against a lower end surface of the piston member and a bottom of the gas bearing and storage tank, and the driving airbag is communicated with the second booster pump. A top of the helium buffer chamber is provided with an injection port and a discharge port. There is at least one second gas pressure sensor, located at a top of an inner chamber of the gas bearing and storage tank. The second gas pressure sensor and the second booster pump are electrically connected to the data processing module 70. The second booster pump drives the driving airbag, and the driving airbag pushes the piston member to adjust a size of the helium buffer chamber, so as to change a sampling volume. Through the movement of the piston member, the gas in the helium buffer chamber is discharged to the chromatographic analyzer 23 for analysis.

Further, the gas sampling and analysis system includes first three-way valve 25 and second three-way valve 26. The first three-way valve 25 is configured to connect the upstream gas sample retention chamber 21, the chromatographic carrier gas cylinder 24, and the second three-way valve 26. The second three-way valve 26 is configured to connect the downstream gas sample retention chamber 22, the first three-way valve 25, and the chromatographic analyzer 23. The first three-way valve 25 and the second three-way valve 26 are controlled to allow the gas in the upstream gas sample retention chamber 21 and the gas in the downstream gas sample retention chamber 22 to enter the chromatographic analyzer 23. Specifically, each of the first three-way valve 25 and the second three-way valve 26 is provided with three connecting ends, namely an a-end, a b-end, and a c-end. For example, the first three-way valve 25 is provided with an a-end connected to the chromatographic carrier gas cylinder 24, a b-end is connected to the upstream gas sample retention chamber 21, and a c-end communicated with an a-end of the second three-way valve 26. The second three-way valve 26 is provided with a b-end connected to the downstream gas sample retention chamber 22 and a c-end connected to the chromatographic analyzer 23.

In analysis, first, the a-end and the c-end of the first three-way valve 25 are communicated, and the a-end and the c-end of the second three-way valve 26 are communicated. The chromatographic carrier gas cylinder 24 is communicated with the chromatographic analyzer 23. Then, the a-end, the b-end, and the c-end of the first three-way valve 25 are communicated. The gas in the upstream gas sample retention chamber 21 is carried by a chromatographic carrier gas to enter the chromatographic analyzer 23. After the analysis of the gas from the upstream gas sample retention chamber 21 is completed, i.e. when only a carrier gas signal is displayed in a chromatogram, the a-end and the c-end of the first three-way valve 25 are communicated, and the upstream gas sample retention chamber 21 is disconnected. The a-end, the b-end, and the c-end of the second three-way valve 26 are communicated, so as to analyze the gas from the downstream gas sample retention chamber 22.

In an optional solution of this embodiment, the device for testing an effective diffusion coefficient of helium in helium-bearing natural gas further includes vacuum pump 80 and fourth control valve 110. The vacuum pump 80 is configured to vacuumize the gas path in the device, or to separately vacuum the upstream gas sample retention chamber 21 and the downstream gas sample retention chamber 22. The fourth control valve 110 is connected to the vacuum pump 80 to control on-off of a gas path of the vacuum pump 80.

In order to ensure separate vacuumizing of the upstream gas sample retention chamber 21 and the downstream gas sample retention chamber 22, in an optional solution of this embodiment, the gas sampling and analysis system further includes third switch valve 27, fourth switch valve 28, and fifth switch valve 29. The third switch valve 27 and the fourth switch valve 28 are connected in series between the upstream gas sample retention chamber 21 and the downstream gas sample retention chamber 22. When vacuumizing the upstream gas sample retention chamber 21 and the downstream gas sample retention chamber 22, the third switch valve 27 and the fourth switch valve 28 are switched on. The fifth switch valve 29 is provided on a tube of the downstream diffusion chamber 12 connected to the vacuum pump 80 to cut off the communication between the vacuum pump 80 and the downstream diffusion chamber 12.

Further, as shown in FIG. 1, the device for testing an effective diffusion coefficient of helium in helium-bearing natural gas includes fourth control valve 110. The fourth control valve 110 is provided on a tube of the upstream diffusion chamber 11 connected to the vacuum pump 80 to cut off the communication between the vacuum pump 80 and the upstream diffusion chamber 11.

Specifically, a vacuumizing process is as follows.

When the entire gas path is vacuumed, the chromatographic carrier gas cylinder 24, the pressure difference balancing argon cylinder 30, and the environmental simulation gas supply cylinder 40 are all closed. The first three-way valve 25 and the second three-way valve 26 can be in any state, while the other valves are turned on to ensure vacuumizing of the gas path.

When the upstream gas sample retention chamber 21 and the downstream gas sample retention chamber 22 are vacuumed separately, the second gas cylinder control valve 100, the third switch valve 27, and the fourth switch valve 28 are turned on. The second control valve 50, the fourth control valve 110, the fifth switch valve 29, and the third control valve 60 are turned off. The first three-way valve 25 is disconnected from the upstream gas sample retention chamber 21, and the second three-way valve 26 is disconnected from the downstream gas sample retention chamber 22. The vacuum pump 80 is turned on. In this way, the upstream and downstream gas sample retention chambers 22 can be vacuumed simultaneously.

In this embodiment, a working process of the diffusion system is as follows.

After the entire gas path is vacuumed, all valves are turned off. Then, the first gas cylinder control valve 90, the second gas cylinder control valve 100, and the fifth switch valve 29 are turned on. In this way, argon is injected into the upstream diffusion chamber 11, and the helium-bearing natural gas is injected into the downstream diffusion chamber 12 to simulate the actual environment. When the differential pressure sensor 14 shows that the gas pressure difference between the upstream diffusion chamber 11 and the downstream diffusion chamber 12 is not greater than 0.1 KPa and the first pressure sensor 19 shows that the gas pressure reaches a required testing pressure, the first gas cylinder control valve 90, the second gas cylinder control valve 100, and the fifth switch valve 29 are turned off. Then, the first switch valve 17 and the second switch valve 18 are turned on to start the diffusion process.

During the diffusion process, the second control valve 50 and the third control valve 60 are turned on for gas sampling. The upstream diffusion chamber 11 is communicated with the upstream gas sample retention chamber 21, and the gas in the upstream diffusion chamber 11 enters the upstream gas sample retention chamber 21. The downstream diffusion chamber 12 is communicated with the downstream gas sample retention chamber 22, and the gas in the downstream diffusion chamber 12 enters the downstream gas sample retention chamber 22.

The first three-way valve 25 and the second three-way valve 26 are controlled for chromatographic analysis.

In an optional solution of this embodiment, the device for testing an effective diffusion coefficient of helium in helium-bearing natural gas further includes a temperature control system. The temperature control system is configured to control the temperature of each valve, each gas sample retention chamber, each diffusion chamber, the true triaxial apparatus 13, and each tube, so as to ensure that the test is carried out at a constant and compliant temperature, ensuring an accurate calculation result. Specifically, the temperature control system can be an insulation box, with various components such as each valve, each gas sample retention chamber, each diffusion chamber, and the true triaxial apparatus 13, etc. provided in the insulation box.

In an optional solution of this embodiment, the data processing module 70 is based on either a personal computer (PC) or an industrial computer. The data processing module is further provided with a serial communication port, a printer, and a scanner to control an operating status of the device, acquire and analyze data, and thus achieve automatic testing.

This embodiment further proposes a method for testing an effective diffusion coefficient of helium in helium-bearing natural gas, using the device for testing an effective diffusion coefficient of helium in helium-bearing natural gas, and including the following steps.

S100, rock core loading. The rock core is put into the true triaxial apparatus 13. A pressure is applied, and the pressure is maintained. A temperature of the rock core is adjusted to a test temperature and is kept constant.

A load pressure is not less than 3 MPa.

S200, vacuumizing. The vacuum pump 80 is started to vacuumize the diffusion system, the gas sampling and analysis system, and the connecting tubes.

S300, gas injection. The pressure difference balancing argon cylinder 30 is opened, and argon is injected into the upstream diffusion chamber 11. The environmental simulation gas supply cylinder 40 is opened, and helium-bearing natural gas for simulating the actual environment is injected into the downstream diffusion chamber 12. When the gas pressures in the upstream diffusion chamber 11 and the downstream diffusion chamber 12 reach a preset value, the pressure difference balancing argon cylinder 30 and the environmental simulation gas supply cylinder 40 are closed.

It should be noted that the gas pressure differences of the upstream diffusion chamber 11 and the downstream diffusion chamber 12 after injection are equal. In actual testing, the gas pressure differences after injection are not greater than 0.1 KPa, and the gas pressures in the upstream diffusion chamber 11 and the downstream diffusion chamber 12 after injection are 0.1-0.5 MPa. In this embodiment, the gas pressures after injection are taken as 0.1 MPa.

S400, gas diffusion. The upstream diffusion chamber 11, the downstream diffusion chamber 12, and the true triaxial apparatus 13 are communicated. Driven by the concentration gradient, the argon in the upstream diffusion chamber 11 diffuses through the rock core to the downstream diffusion chamber 12, and the helium-bearing natural gas in the downstream diffusion chamber 12 diffuses through the rock core to the upstream diffusion chamber 11.

S500, gas sampling and analysis. During the diffusion process, the vacuum pump 80 is turned on to vacuumize the upstream gas sample retention chamber 21 and the downstream gas sample retention chamber 22. The vacuum pump 80 is turned off. The second control valve 50 is turned on to allow the gas in the upstream diffusion chamber 11 to enter the upstream gas sample retention chamber 21, and the third control valve 60 is turned on to allow the gas in the downstream diffusion chamber 12 to enter the downstream gas sample retention chamber 22. The second control valve 50 and the third control valve 60 are turned off. The compositions of a mixed gas in the upstream gas sample retention chamber 21 and the compositions of the mixed gas in the downstream gas sample retention chamber 22 are respectively analyzed through the chromatographic analyzer 23. This step is repeated at least five times to acquire at least five groups of data on the compositions of the mixed gas, and the data, acquired at last two times, on the compositions of the mixed gas are identical, so as to confirm the completion of the gas diffusion process.

It should be noted that the gas is sampled for a first time 5 hours after diffusion begins, and the gas is taken every 5 hours. The specific time interval is determined based on an actual situation. The number of sampling times is determined according to an actual need, and it may be less than 5 times, until the completion of the gas diffusion process is confirmed. Meanwhile, the chromatographic carrier gas cannot be the same as the test gas.

S600, diffusion coefficient calculation. According to Fick's second law, effective diffusion coefficient $D_i$ of an i-th gas in the helium-bearing natural gas is calculated as follows:

$$D_i = a \frac{L}{A} \left( \frac{1}{1/V_{upstream} + 1/V_{downstream}} \right), \tag{1}$$

where,

L denotes a length of the rock core, which means that the gas diffuses along a length direction of the rock core;

A denotes a cross-sectional area of the rock core, which is a cross-sectional area through which the gas passes;

$V_{upstream}$ denotes a volume of the upstream diffusion chamber 11;

$V_{downstream}$ denotes a volume of the downstream diffusion chamber 12;

α denotes a concentration decline index of the i-th gas, calculated as follows:

$$a = \ln\left(\frac{\Delta C_0}{\Delta C_t}\right) / \Delta t, \tag{2}$$

where, $\Delta C_0$ denotes a concentration difference of the i-th gas in the upstream diffusion chamber 11 and the downstream diffusion chamber 12 at time $t_0$ during the diffusion process;

$\Delta C_t$ denotes a concentration difference of the i-th gas in the upstream diffusion chamber 11 and the downstream diffusion chamber 12 at time t during the diffusion process; and $\Delta t$ denotes a diffusion time, $\Delta t = t - t_0$.

In the diffusion process, a natural logarithm of a ratio of the concentration difference at the initial time $t_0$ to the concentration difference at the time t is linear with the diffusion time $\Delta t$.

According to equations (1) and (2), $$\ln\left(\frac{\Delta C_0}{\Delta C_t}\right) = D_i E t - D_i E t_0, \quad (3)$$

where, $E = A(1/V_{upstream} + 1/V_{downstream})/L$ is a constant.

According to equation (3), slope k is acquired by fitting through a least squares method.

Finally, the effective diffusion coefficient of the i-th gas in the helium-bearing natural gas is $D_i = k/E$.

It should be noted that each of the volume of the upstream diffusion chamber 11 and the volume of the downstream diffusion chamber 12 includes a volume of a tube connected.

Obviously, this device can also be used to test the diffusion coefficients of other components in the helium-bearing natural gas, and is not limited to a specific gas. Therefore, the device is also suitable for other types of mixed gases, not limited to the helium-bearing natural gas.

The present disclosure simulates the diffusion process of helium-bearing natural gas in a geological environment through the diffusion system, and acquires gas samples for analysis through the gas sampling and analysis system during the diffusion process. Finally, the present disclosure calculates the effective diffusion coefficient of the helium in helium-bearing natural gas. Therefore, the present disclosure provides a comprehensive device and method for calculating the diffusion coefficient of helium in helium-bearing natural gas, quantitatively characterizing the diffusion behavior of helium in helium-bearing natural gas.

Finally, it should be noted that the above examples are merely intended to describe the technical solutions of the present disclosure, rather than to limit the present disclosure. Although the present disclosure is described in detail with reference to the above examples, persons of ordinary skill in the art should understand that modifications may be made to the technical solutions described in the above examples or equivalent replacements may be made to some or all technical features thereof, which do not make the essence of corresponding technical solutions depart from the scope of the technical solutions in the examples of the present disclosure.

What is claimed is:

1. A device for testing an effective diffusion coefficient of helium in helium-bearing natural gas, comprising:
   a diffusion system and a gas sampling and analysis system, wherein
   the diffusion system comprises an upstream diffusion chamber, a downstream diffusion chamber, and a true triaxial apparatus; and two ends of the true triaxial apparatus are respectively connected to the upstream diffusion chamber and the downstream diffusion chamber;
   the upstream diffusion chamber is filled with argon, and the downstream diffusion chamber is filled with helium-bearing natural gas for simulating an actual environment; and the true triaxial apparatus is configured to accommodate a rock core, apply a load to the rock core, and simulate a formation temperature;
   the gas sampling and analysis system comprises an upstream gas sample retention chamber, a downstream gas sample retention chamber, and a chromatographic analyzer;
   the upstream gas sample retention chamber is connected to the upstream diffusion chamber to sample the gas in the upstream diffusion chamber; and the downstream gas sample retention chamber is connected to the downstream diffusion chamber to sample the gas in the downstream diffusion chamber;
   an initial state of the upstream gas sample retention chamber and the downstream gas sample retention chamber is a vacuum state for convenience of gas sampling;
   the chromatographic analyzer is configured to analyze gas composition in the upstream gas sample retention chamber and the downstream gas sample retention chamber;
   the true triaxial apparatus comprises pressure plates, sealing strips, a pressure block, a pressure chamber, a hydraulic cylinder, and a hydraulic bag;
   the pressure plates are provided inside the pressure chamber, and the pressure plates are abutted against the rock core to apply a pressure to the rock core;
   adjacent pressure plates are separated by the sealing strip; and the pressure plates and the sealing strips enclose a rock core accommodation chamber;
   the pressure block comprises a first end connected to the pressure plate and a second end connected to the hydraulic bag; and the hydraulic bag is expanded to push the pressure block to move towards the rock core;
   the pressure block comprises the first end connected to the pressure plate and the second end connected to the hydraulic cylinder;
   the hydraulic bag is a hollow cylindrical structure with a rectangular axial section, and the hydraulic bag is embedded in the pressure chamber; and the hydraulic bag is provided between the pressure block and the pressure chamber;
   each of the sealing strips comprises an arc segment, a positioning segment, and a reinforced sealing segment; the arc segment comprises a front end surface connected to the reinforced sealing segment and a rear end surface connected to the positioning segment; and the arc segment, the positioning segment, and the reinforced sealing segment are distributed coaxially;
   a plurality of ellipsoidal deformation cavities parallel to an axis of the sealing strip are uniformly distributed inside the arc segment, the positioning segment, and the reinforced sealing segment; and at least two ellipsoidal deformation cavities perpendicular to the axis of the sealing strip are arranged at each of a connection position between a first end of the arc segment and the positioning segment and a connection position between a second end of the arc segment and the reinforced sealing segment;
   the upstream diffusion chamber is structurally identical to the downstream diffusion chamber, and the upstream diffusion chamber comprises a gas storage cylinder and a distribution tube;
   the upstream gas sample retention chamber is structurally identical to the downstream gas sample retention chamber, and the upstream gas sample retention chamber comprises a gas bearing and storage tank, a piston member, and a driving airbag; the piston member is embedded in the gas bearing and storage tank and slidably connected to an inner side of the gas bearing and storage tank; the piston member is coaxial with the gas bearing and storage tank, and the piston member divides the gas bearing and storage tank into a helium buffer chamber and a regulating chamber along an axial direction; and the driving airbag is embedded in the regulating chamber, and the driving airbag pushes the piston member to adjust a size of the helium buffer chamber; and the diffusion system further comprises a differential pressure sensor; and two ends of the differential pressure sensor are respectively connected to the upstream diffusion chamber and the downstream diffusion chamber to detect a gas pressure difference between the upstream diffusion chamber and the downstream diffusion chamber.

2. The device for testing the effective diffusion coefficient of helium in helium-bearing natural gas according to claim 1, further comprising a pressure difference balancing argon cylinder and an environmental simulation gas supply cylinder, wherein the pressure difference balancing argon cylinder is connected to the upstream diffusion chamber to inject the argon into the upstream diffusion chamber; and the environmental simulation gas supply cylinder is connected to the downstream diffusion chamber to inject the helium-bearing natural gas for simulating the actual environment into the downstream diffusion chamber.

3. The device for testing the effective diffusion coefficient of helium in helium-bearing natural gas according to claim 2, wherein the diffusion system further comprises a transfer tube and a first control valve;

the transfer tube is connected in parallel with the differential pressure sensor; and two ends of the transfer tube are respectively connected to the upstream diffusion chamber and the downstream diffusion chamber; and the first control valve is provided on the transfer tube to control switching-on/off of the transfer tube.

4. The device for testing the effective diffusion coefficient of helium in helium-bearing natural gas according to claim 3, further comprising a second control valve and a third control valve, wherein the second control valve is provided between the upstream diffusion chamber and the upstream gas sample retention chamber to control switching-on/off of the upstream diffusion chamber and the upstream gas sample retention chamber; and the third control valve is provided between the downstream diffusion chamber and the downstream gas sample retention chamber to control switching-on/off of the downstream diffusion chamber and the downstream gas sample retention chamber.

5. The device for testing the effective diffusion coefficient of helium in helium-bearing natural gas according to claim 4, further comprising a vacuum pump, wherein the vacuum pump is connected to the diffusion system and the gas sampling and analysis system to vacuumize the diffusion system, the gas sampling and analysis system, and a connecting tube.

6. The device for testing the effective diffusion coefficient of helium in helium-bearing natural gas according to claim 5, wherein the true triaxial apparatus further comprises an electric heating wire; and the electric heating wire is provided at a side of the pressure plate to adjust a temperature of the rock core, wherein the side of the pressure plate is away from the rock core.

7. The device for testing the effective diffusion coefficient of helium in helium-bearing natural gas according to claim 6, further comprising a first booster pump, wherein the first booster pump is connected to the hydraulic bag to drive the hydraulic bag to expand, so as to push the pressure block to move towards the rock core.

8. The device for testing the effective diffusion coefficient of helium in helium-bearing natural gas according to claim 7, wherein the gas sampling and analysis system further comprises a chromatographic carrier gas cylinder; and the chromatographic carrier gas cylinder is connected to the upstream gas sample retention chamber, the downstream gas sample retention chamber and the chromatographic analyzer to carry the gas in the upstream gas sample retention chamber and the gas in the downstream gas sample retention chamber into the chromatographic analyzer.

9. A method for testing an effective diffusion coefficient of helium in helium-bearing natural gas, using the device for testing the effective diffusion coefficient of helium in helium-bearing natural gas according to claim 8, and comprising the following steps:

rock core loading: putting the rock core into the true triaxial apparatus; applying a pressure, and maintaining the pressure; and adjusting a temperature of the rock core to a test temperature, and keeping the temperature constant;

vacuumizing: starting the vacuum pump to vacuumize the diffusion system, the gas sampling and analysis system, and the connecting tube;

gas injection: opening the pressure difference balancing argon cylinder to inject the argon into the upstream diffusion chamber; opening the environmental simulation gas supply cylinder to inject the helium-bearing natural gas for simulating the actual environment into the downstream diffusion chamber; and closing the pressure difference balancing argon cylinder and the environmental simulation gas supply cylinder when a gas pressure in the upstream diffusion chamber and a gas pressure in the downstream diffusion chamber reach a preset value;

gas diffusion: communicating the upstream diffusion chamber, the downstream diffusion chamber, and the true triaxial apparatus; and allowing, under an action of a concentration gradient, the argon in the upstream diffusion chamber to diffuse through the rock core to the downstream diffusion chamber and the helium-bearing natural gas in the downstream diffusion chamber to diffuse through the rock core to the upstream diffusion chamber;

gas sampling and analysis: turning, during a diffusion process, the vacuum pump on to vacuumize the upstream gas sample retention chamber and the downstream gas sample retention chamber, and then turning the vacuum pump off; turning the second control valve on to allow the gas in the upstream diffusion chamber to enter the upstream gas sample retention chamber, and turning the third control valve on to allow the gas in the downstream diffusion chamber to enter the downstream gas sample retention chamber; then, turning the second control valve and the third control valve off; analyzing, through the chromatographic analyzer, compositions of a mixed gas in the upstream gas sample retention chamber and compositions of the mixed gas in the downstream gas sample retention chamber, respectively; and repeating this step at least five times to acquire at least five groups of data on the compositions of the mixed gas, wherein the data, acquired at last two times, on the compositions of the mixed gas are identical; and diffusion coefficient calculation: calculating, according to Fick's second law, an effective diffusion coefficient $D_i$ of an i-th gas in the helium-bearing natural gas as follows:

$$D_i = a\frac{L}{A}\left(\frac{1}{1/V_{upstream} + 1/V_{downstream}}\right), \tag{1}$$

wherein,
L denotes a length of the rock core;
A denotes a cross-sectional area of the rock core;
$V_{upstream}$ denotes a volume of the upstream diffusion chamber;
$V_{downstream}$ denotes a volume of the downstream diffusion chamber;
α denotes a concentration decline index of the i-th gas, and α is calculated as follows:

$$a = \ln\left(\frac{\Delta C_0}{\Delta C_t}\right)/\Delta t, \tag{2}$$

wherein, $\Delta C_0$ denotes a concentration difference of the i-th gas in the upstream diffusion chamber and the downstream diffusion chamber at an initial time $t_0$ during the diffusion process;

$\Delta C_t$ denotes a concentration difference of the i-th gas in the upstream diffusion chamber and the downstream diffusion chamber at a time t during the diffusion process; and $\Delta t$ denotes a diffusion time, $\Delta t = t - t_0$;

in the diffusion process, a natural logarithm of a ratio of the concentration difference at the initial time $t_0$ to the concentration difference at the time t is linear with the diffusion time $\Delta t$;

therefore, according to equations (1) and (2), $$\ln\left(\frac{\Delta C_0}{\Delta C_t}\right) = D_i Et - D_i Et_0, \tag{3}$$

wherein, $E = A(1/V_{upstream} + 1/V_{downstream})/L$ is a constant.

according to equation (3), a slope k is acquired by fitting through a least squares method; and finally, the effective diffusion coefficient of the i-th gas in the helium-bearing natural gas is $D_i = k/E$.

* * * * *